United States Patent
Matani et al.

(10) Patent No.: US 11,311,328 B2
(45) Date of Patent: Apr. 26, 2022

(54) HIGH-PRESSURE STEAM-BASED SURGICAL TOOL FOR CUTTING AND HEMOSTASIS

(71) Applicant: Imam Abdulrahman Bin Faisal University, Dammam (SA)

(72) Inventors: Abdelaziz Matani, Dammam (SA); Mutasem Samih Matani, Dammam (SA); Ahmed Abdelkarim Mansi, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 905 days.

(21) Appl. No.: 15/981,023

(22) Filed: May 16, 2018

(65) Prior Publication Data
US 2019/0350614 A1   Nov. 21, 2019

(51) Int. Cl.
*A61B 18/04* (2006.01)
*A61B 17/32* (2006.01)
(Continued)

(52) U.S. Cl.
CPC .......... *A61B 18/04* (2013.01); *A61B 17/3203* (2013.01); *A61B 17/320016* (2013.01); *A61B 2017/00084* (2013.01); *A61B 2017/00349* (2013.01); *A61B 2017/00367* (2013.01); *A61B 2017/00477* (2013.01);
(Continued)

(58) Field of Classification Search
CPC ....... A61B 2017/1648; A61B 17/3203–32037; A61B 2018/00017; A61B 2018/044; A61B 2018/046; A61B 2018/048; A61B 2017/2926; A61B 2017/00367; A61B 2017/00477; A61B 2017/00862
See application file for complete search history.

(56) References Cited

U.S. PATENT DOCUMENTS

| | | | |
|---|---|---|---|
| 2002/0177846 A1* | 11/2002 | Mulier | A61B 18/04 606/27 |
| 2005/0103819 A1* | 5/2005 | Racenet | A61B 17/068 227/175.1 |

(Continued)

FOREIGN PATENT DOCUMENTS

WO    2003/096871 A2    11/2003

OTHER PUBLICATIONS

Nakano, Toru, et al.; Use of water jet instruments in gastrointestinal endoscopy; Feb. 10, 2016; features 1 2 and 3; https://www.ncbi.nlm.nih.gov/pmc/articles/PMC4734971/.

*Primary Examiner* — Jaymi E Della
*Assistant Examiner* — Sean W Collins
(74) *Attorney, Agent, or Firm* — Oblon, McClelland, Maier & Neustadt, L.L.P.

(57) ABSTRACT

The present disclosure relates to a surgical tool for cutting and hemostasis of biological tissues. The surgical tool includes a hollow blade comprising a cutting implement residing within a hollow cavity configured to provide high-pressure steam through an apical surface. The cutting implement can operate independently or in cooperation with the provided high-pressure steam. The surgical tool of the present disclosure applies a directionally-controlled, high-pressure steam flow to a tissue region of interest. A control unit provides temperature-controlled steam at a flow-rate determined in accordance with tissue type and intended procedure.

8 Claims, 11 Drawing Sheets

(51) Int. Cl.
*A61B 17/3203* (2006.01)
*A61B 17/00* (2006.01)
*A61B 18/00* (2006.01)
*A61B 17/29* (2006.01)

(52) U.S. Cl.
CPC ............... *A61B 2017/00862* (2013.01); *A61B 2017/00991* (2013.01); *A61B 2017/2926* (2013.01); *A61B 2018/00017* (2013.01); *A61B 2018/00029* (2013.01); *A61B 2018/00041* (2013.01); *A61B 2018/0091* (2013.01); *A61B 2018/00101* (2013.01); *A61B 2018/00172* (2013.01); *A61B 2018/00494* (2013.01); *A61B 2018/00577* (2013.01); *A61B 2018/00589* (2013.01); *A61B 2018/00714* (2013.01); *A61B 2018/00791* (2013.01); *A61B 2018/048* (2013.01)

(56) References Cited

U.S. PATENT DOCUMENTS

| | | | |
|---|---|---|---|
| 2010/0114082 A1 | 5/2010 | Sharma | |
| 2012/0203270 A1* | 8/2012 | Chen | A61B 17/29 606/205 |
| 2014/0005705 A1* | 1/2014 | Weir | A61B 17/320092 606/169 |
| 2014/0288543 A1* | 9/2014 | Hoey | A61B 18/04 606/27 |
| 2016/0302820 A1* | 10/2016 | Hibner | A61B 17/320092 |

* cited by examiner

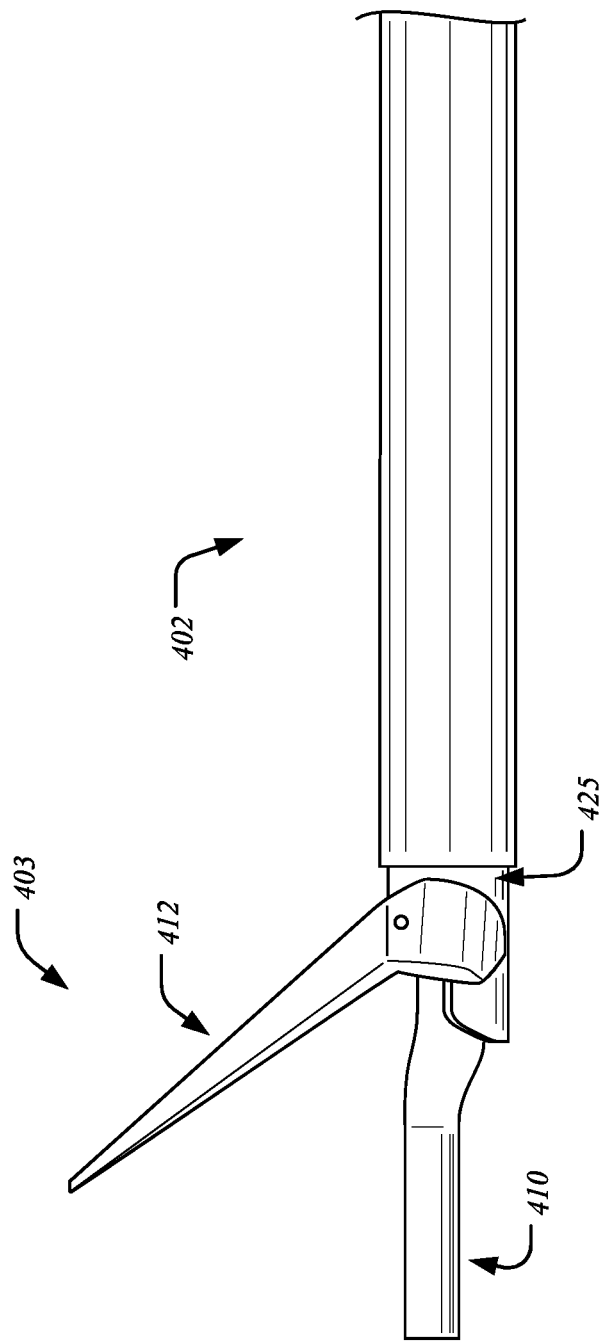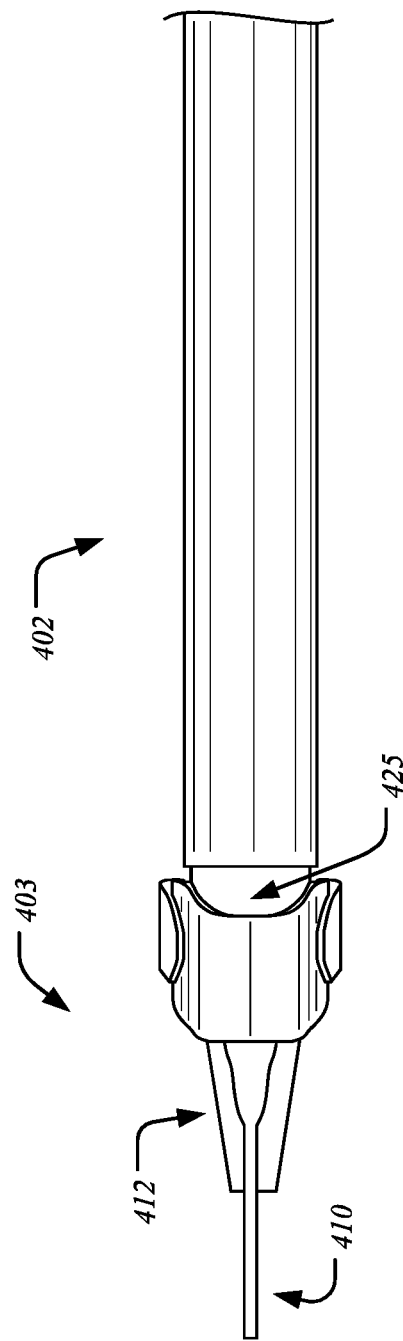

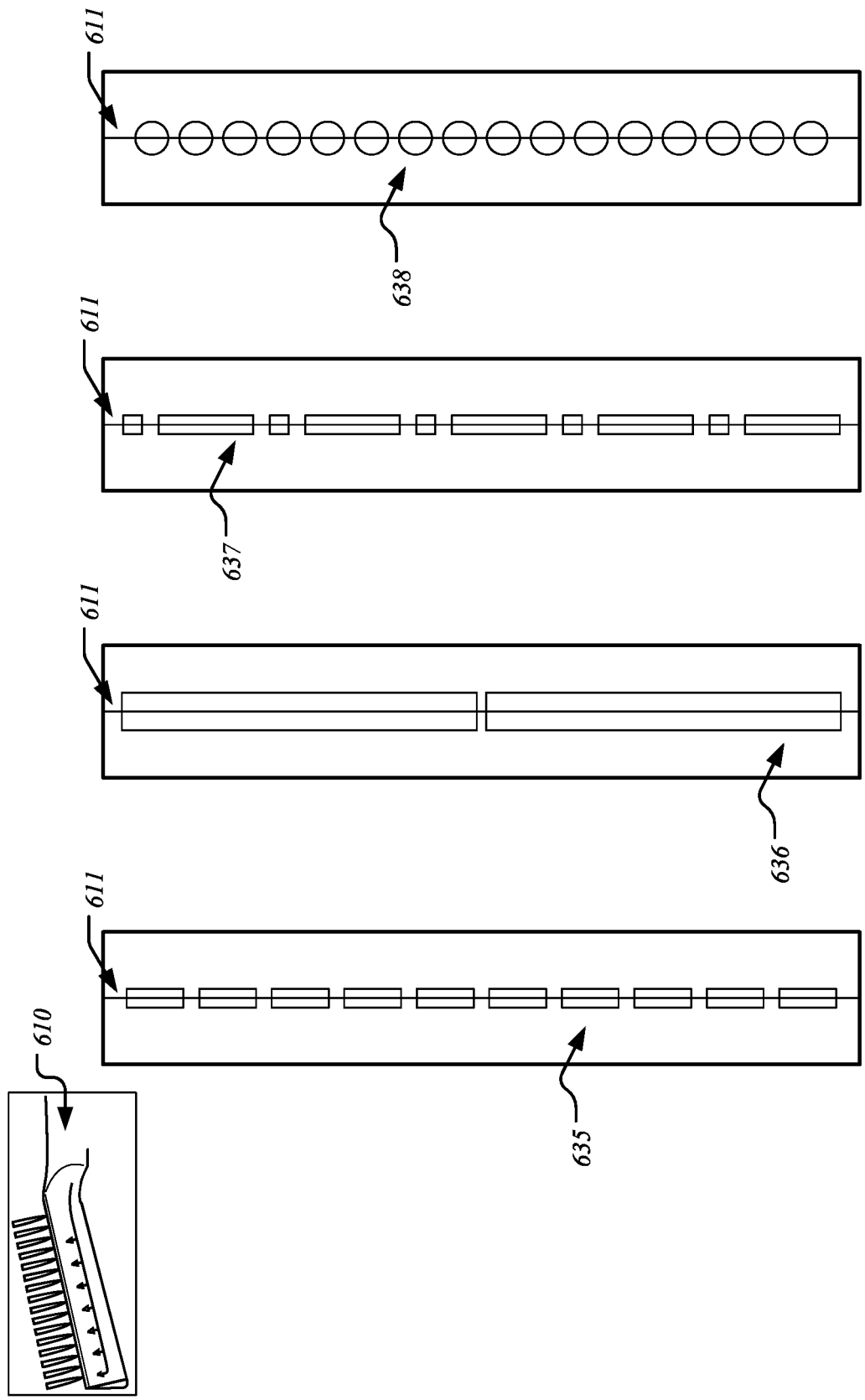

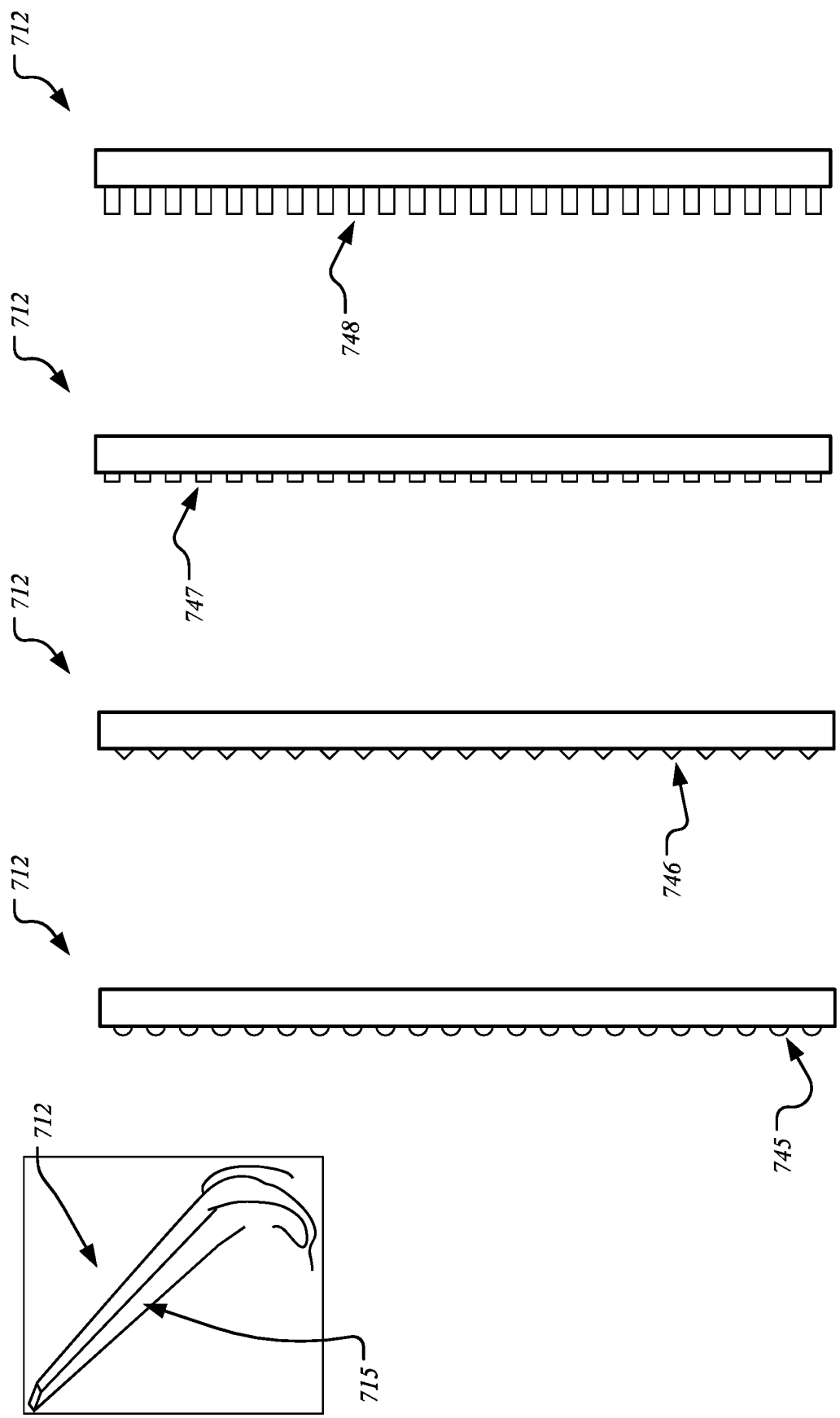

HIGH-PRESSURE STEAM-BASED SURGICAL TOOL FOR CUTTING AND HEMOSTASIS

BACKGROUND

Field of the Disclosure

The present disclosure relates to a high-pressure steam-based surgical tool for endoscopic surgical procedures.

Description of the Related Art

Endoscopy, a procedure allowing doctors to visualize internal organs and structures of the human body without large superficial incisions, makes it possible to better investigate symptoms and diagnose disease, most commonly involving the gastrointestinal tract. This approach, however, can be further applied to other organs or structures including, but not limited to, the abdomen, cervix, and thorax. While providing visual access to internal structures without open surgery, endoscopy naturally limits the surgeon's toolkit with regard to the control of internal bleeding, an inherent complication associated with small, deep incisions made during endoscopic procedures. Traditional approaches employ heated electrical wires or freezing via liquid nitrogen, however, each approach carries with it a set of safety concerns and risk factors, including adverse heating or cooling of off-target tissues and nerve damage. Intended to address these concerns, high-pressure liquid has been proposed for cutting, dissecting, abrading and/or hemostasis. While effective in specific applications, the use of high-pressure liquids may result in tissue shearing. Further, a lack of directional control may lead to off-target application. See "Multipurpose fluid jet surgical device" by Adrian, PAZ, (WO2003096871A2). Therefore, a safe and effective endoscopic surgical tool for cutting and hemostasis need be developed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a surgical tool for incision and hemostasis of biological tissues. The surgical tool includes a head element comprising an assisting element and an operative element. The operative element, or hollow blade, comprises a cutting implement residing within a hollow cavity configured to provide high-pressure steam through one or more ports at an apical surface. The cutting implement can operate independently or in cooperation with the provided high-pressure steam. Further, the hollow blade can operate independently or in cooperation with the assisting element, or grasping element, to hold or cut target tissues. The head element of the present disclosure is rotatable.

According to an embodiment, the one or more ports of the operative element allow for a controlled, directional application of the steam flow. A control unit provides temperature-controlled steam at a flow-rate determined in accordance with tissue type and intended procedure.

According to an embodiment, the operative element and assisting element may be shaped in a procedure-specific manner to allow improved access to hidden internal structures.

In an embodiment, the operative element and assistant element are fabricated into a desired shape. In another embodiment, a plurality of user-controlled wires applies a deformational force to the head element to produce a desired curvature in the operative element and the assisting element.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 4A is an exemplary illustration of an orientation of the head element of the surgical tool, according to an embodiment of the present disclosure;

FIG. 4B is an exemplary illustration of an orientation of the head element of the surgical tool, according to an embodiment of the present disclosure;

FIG. 6A is an exemplary illustration of a configuration of steam ports on an operative element of the surgical tool, according to an embodiment of the present disclosure;

FIG. 6B is an exemplary illustration of a configuration of steam ports on an operative element of the surgical tool, according to an embodiment of the present disclosure;

FIG. 6C is an exemplary illustration of a configuration of steam ports on an operative element of the surgical tool, according to an embodiment of the present disclosure;

FIG. 6D is an exemplary illustration of a configuration of steam ports of an operative element of the surgical tool, according to an embodiment of the present disclosure;

FIG. 7A is an exemplary illustration of a configuration of an assisting element of the surgical tool, according to an exemplary embodiment of the present disclosure;

FIG. 7B is an exemplary illustration of a configuration of an assisting element of the surgical tool, according to an exemplary embodiment of the present disclosure;

FIG. 7C is an exemplary illustration of a configuration of an assisting element of the surgical tool, according to an exemplary embodiment of the present disclosure;

FIG. 7D is an exemplary illustration of a configuration of an assisting element of the surgical tool, according to an exemplary embodiment of the present disclosure;

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Currently, endoscopic surgery is complicated by the risk of uncontrollable, internal bleeding as conventional cutting implements do not directly address the consequences of an incision. Surgeons, therefore, have employed heated electric wires during surgery, or circumvented this complication entirely, with cryotherapy employing liquid nitrogen. Each approach carries with it a set of risks and limitations and creates a need for an approach with an improved efficacy and safety profile.

To this end, the present disclosure describes a device comprising an operative element and an assisting element. The operative element includes a cutting implement and one or more ports for the delivery of steam, wherein the steam is heated to a pre-determined temperature and delivered at a pre-determined flow strength, such that the device performs internal tissue cutting while simultaneously coagulating tissue injuries created during the incision. In this way, a controlled and localized burning of the tissue achieves hemostasis.

Figure 1:
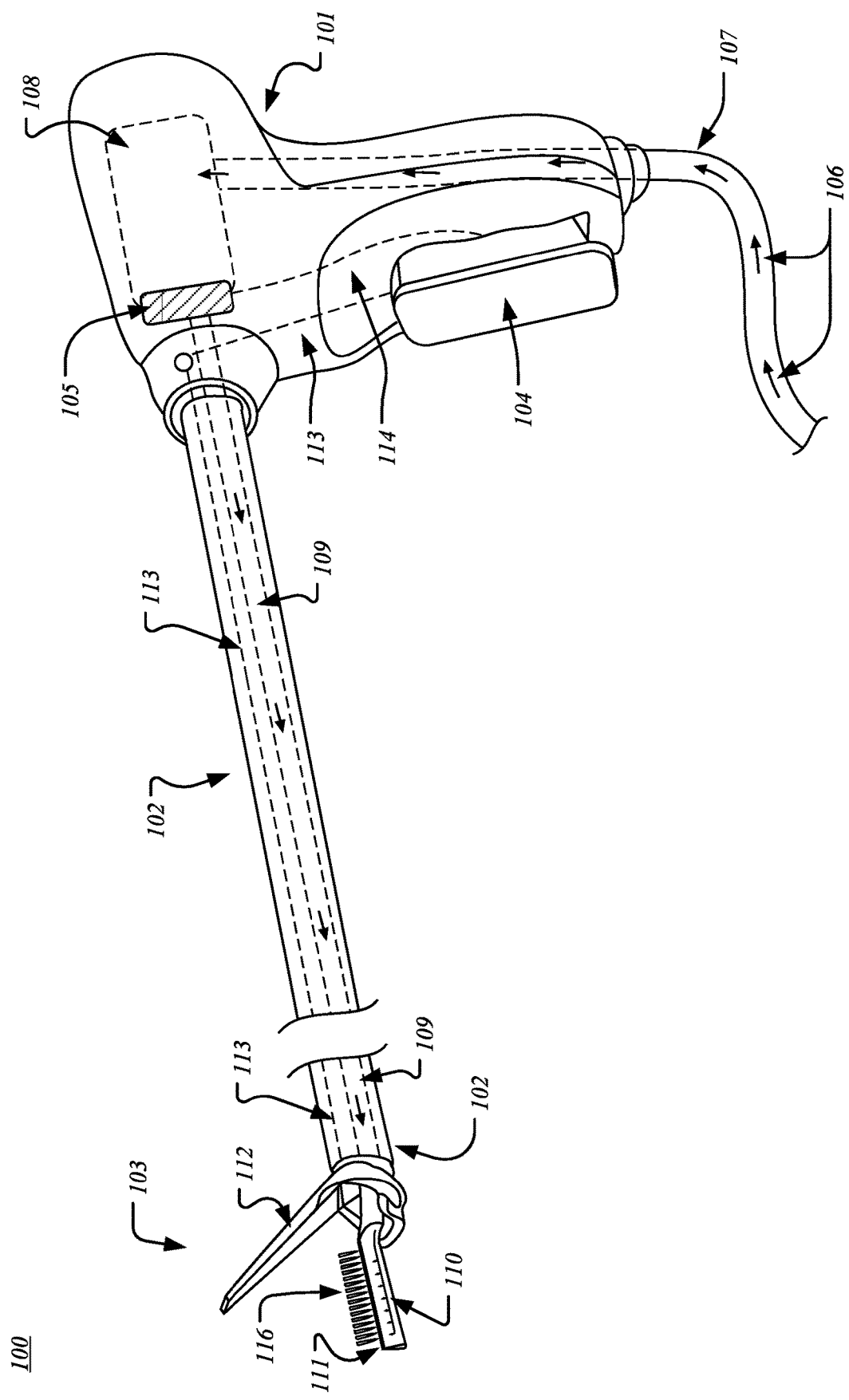
FIG. 1 is an exemplary illustration of a surgical tool, according to an embodiment of the present disclosure.

FIG. 1 is an exemplary illustration of a surgical tool, according to an embodiment of the present disclosure. The surgical tool 100 includes a handle 101, a hollow tube 102 and a head element 103. The handle 101 further comprises a steam canister 108 and a trigger 104 connected to a steam valve 105. The trigger 104 is connected to the steam valve 105 via valve wire 114. The steam canister 108 is in fluid communication with a steam tube 107 that provides pressurized steam 106 to the surgical tool 100. The trigger 104 is further connected to an assisting element, referred to herein as a movable jaw 112, via a jaw wire 113.

Adjacent to the handle 101 is the hollow tube 102. In another embodiment, the hollow tube 102 is a catheter. The hollow tube 102 can be telescopic or of variable fixed-lengths, according to the requirements of a procedure. The hollow tube 102 comprises the steam channel 109 and a segment of the jaw wire 113. The diameter of the hollow tube 102, and the steam channel 109 and jaw wire 113 therein, can be a range of sizes appropriate as determined for an intended procedure. In an embodiment, the hollow tube 102 is of sufficient size wherein the lumen further comprises complementary surgical tools, including, but not limited to, imaging tools for guided surgery. The head element 103 is disposed at a distal end of the hollow tube 102. The head element 103 comprises a moveable jaw 112 and an operative element, referred to herein as a hollow blade 110. The steam flow 106 travels from the steam canister 108 through the steam channel 109 to the hollow blade 110, where it exits on opposing surfaces of a cutting implement 111 to form steam streams 115.

According to an embodiment, the handle 101 of the surgical tool 100 is fabricated of a temperature resistant synthetic material such as polyetherimide, a semi-transparent high strength plastic material that can operate in high temperature environments. In other embodiments, the handle 101 may be fabricated of any suitable material that can be sterilized, including, but not limited to polypropylene, polysulfone, polyether ether ketone, stainless steel, or a combination thereof.

According to an embodiment, the hollow tube 102, steam tube 107, and steam channel 109 of the surgical tool 100 may be fabricated of elastomeric materials typical of devices used in endoscopy, including, but not limited to, polyurethanes, polyesters, or a combination thereof.

According to an embodiment, the head element 103 of the surgical tool 100 may be fabricated of a temperature resistant synthetic material such as polyetherimide, a semi-transparent high strength plastic material that can operate in high temperature environments. In other embodiments, the head element 103 may be fabricated of any suitable material that can be sterilized, including, but not limited to polypropylene, polysulfone, polyether ether ketone, stainless steel, or a combination thereof.

According to an embodiment, the cutting implement 111 of the surgical tool 100 is a blade of a type known in the art as standard for surgical incisions. In another embodiment, the cutting implement 111 is fabricated of a semi-rigid plastic, metal, or combination thereof, and is configured to bend under manual operation by a user. The cutting implement 111 and hollow blade 110 may be fabricated for one-time use or repeated use.

In an embodiment, each component of the surgical tool 100 is thermally insulated to provide temperature control throughout the surgical procedure and to insulate surrounding tissue from excess heating. Isolating the heat internal to the surgical tool 100 eliminates concern for off-target heating as the temperature of the exterior of the device might be elevated in accordance with the temperature of the steam in the steam tube, steam canister, and steam channel.

In an exemplary embodiment, the steam flow 106 is collected in the steam canister 108. When appropriate, the trigger 104 is engaged and, simultaneously, the jaw wire 113 and valve wire 114 activate the movable jaw 112 and the valve 105, respectively. As steam flow 106 travels from the steam canister 108 through the steam channel 109 and into the hollow blade 110 of the head element 103, the movable jaw 112 is engaged in the direction of the cutting implement 111. While the movable jaw 112 aids in controlling the position of a tissue of interest with respect to the cutting implement 111, the steam flow 106 exits the hollow blade 110 and becomes at least one of a series of steam streams 116 of a pre-determined number, distribution, and shape. Following the incision of the target tissue created as the cutting implement 111 comes into contact with a surface of the movable jaw 112, the steam streams 116 seal the open ends of the tissue left by the incision.

Figure 2B:
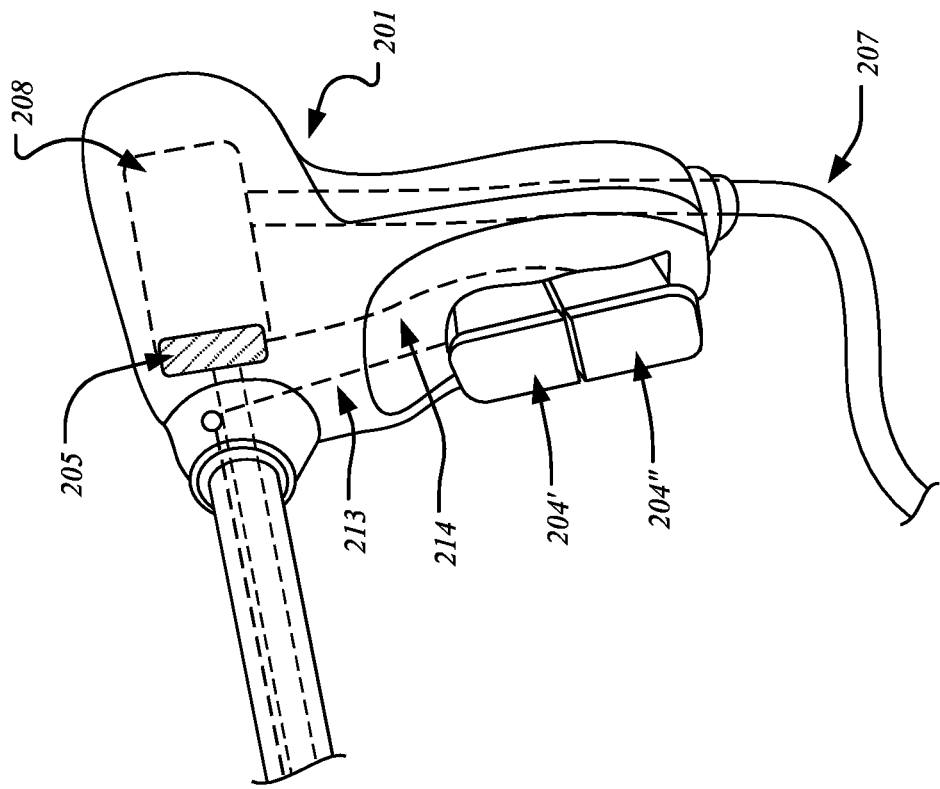
FIG. 2B is an exemplary illustration of a handle of the surgical tool, according to an embodiment of the present disclosure.
Figure 2A:
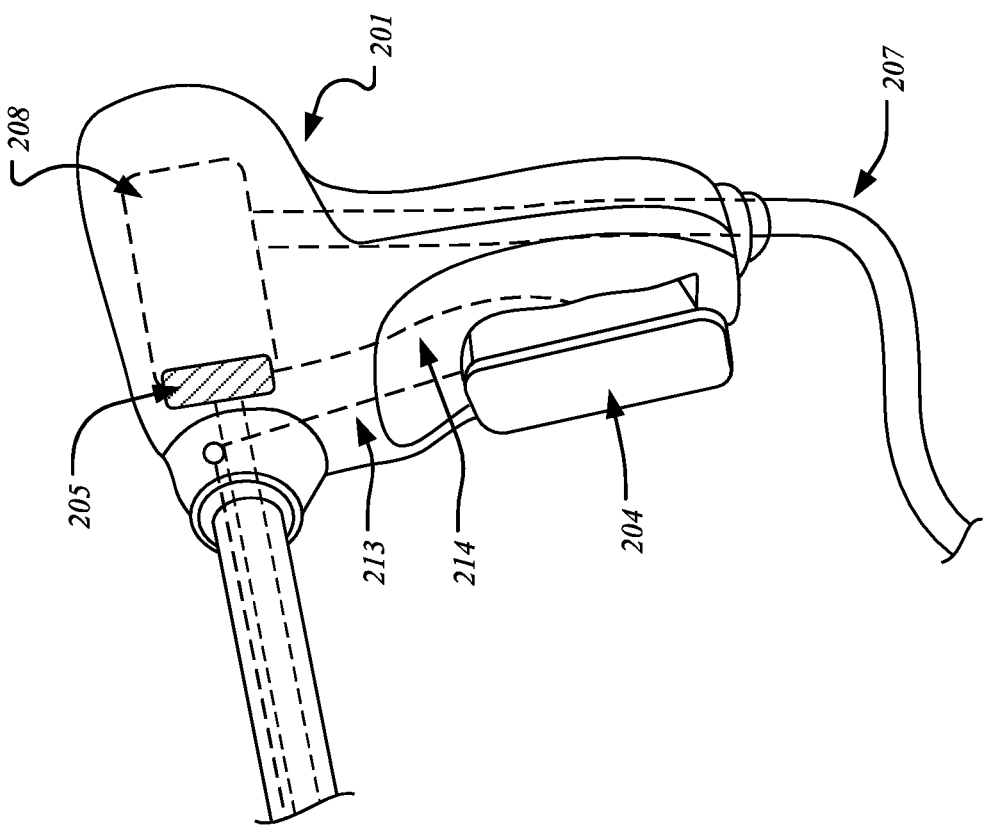
FIG. 2A is an exemplary illustration of a handle of the surgical tool, according to an embodiment of the present disclosure.

FIG. 2A and FIG. 2B are exemplary illustrations of the handle of the surgical tool, according to an embodiment of the present disclosure. In an embodiment, the trigger 204 is a single trigger responsible for engaging both the movable jaw of the head element of the surgical tool and the steam valve 205 of the handle 201 simultaneously. In another embodiment, it is preferable to have independent control of the movable jaw of the head element and the steam valve of the handle. The jaw wire 213 is connected to a first trigger 204' and the valve wire 214 is connected to a second trigger 204". If it is desirable to only incise the tissue of interest, the first trigger 204' may be engaged independently of the second trigger 204". If it is desirable to only employ steam for tissue sealing, the second trigger 204" may be engaged independently of the first trigger 204'. In both instances, a steam tube 207 supplies a steam flow to a steam canister 208 for storage.

According to an embodiment, the handle 201 is further modified to provide additional functionality. In an exemplary embodiment, the handle 201 includes a plurality of triggers directed to rotational control of the head element of the surgical tool. In another embodiment, the handle 201 further comprises, but is not limited to, imaging tools for guided surgery and a power supply to enhance functionality of, and user interfacing with, the handle 201.

Figure 3A:
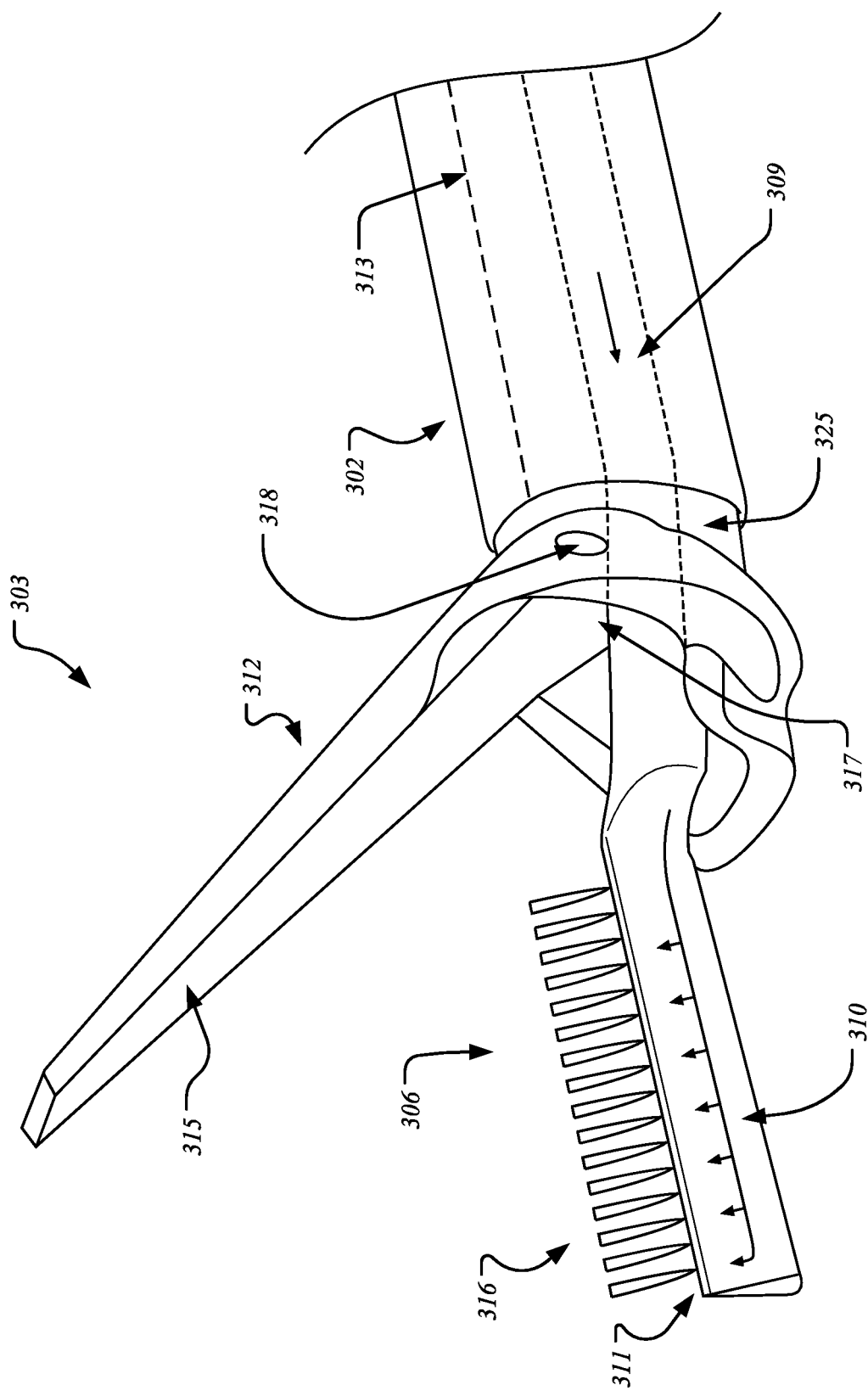
FIG. 3A is an exemplary illustration of a head element of the surgical tool, according to an embodiment of the present disclosure.

FIG. 3A is an exemplary illustration of a head element 303 of the surgical tool, according to an embodiment of the present disclosure. Extending from the hollow tube 302, a jaw wire 313 is functionally attached to a movable jaw 312. A steam channel 309 also extends from the hollow tube 302 and is in fluid communication with a hollow blade 310. The hollow blade 310 comprises a cutting implement 311 and steam ports for steam 306. The steam 306 exits the hollow blade 310 through the steam ports as steam streams 316. During operation, the movable jaw 312 is rotated towards the cutting implement 311, in an action typical of scissors. Simultaneously to the implementation of the cutting implement 311, the steam streams 316 exit the hollow blade 310 across opposing faces of the cutting implement 311.

According to an embodiment, the hollow tube 302 further comprises, but is not limited to, imaging tools for guided surgery. Extending from the hollow tube 302, the imaging tools for guided surgery may then be disposed in a variety of positions. These positions may include, but are not limited to, the face 315 of the movable jaw 312 or the exit of the hollow tube 317, wherein the utilization of the cutting implement 311 and the steam streams 316 may be monitored.

In an embodiment, the head element 303 of the surgical tool is disposed on a coupler 325 that is concentric with the hollow tube 302. The coupler 325 is of an outer diameter relatively smaller than the inner diameter of the hollow tube 302. In an embodiment, the movable jaw 312 is attached to the coupler 325 at pin 318, allowing for rotation about the pin 318.

Figure 3B:
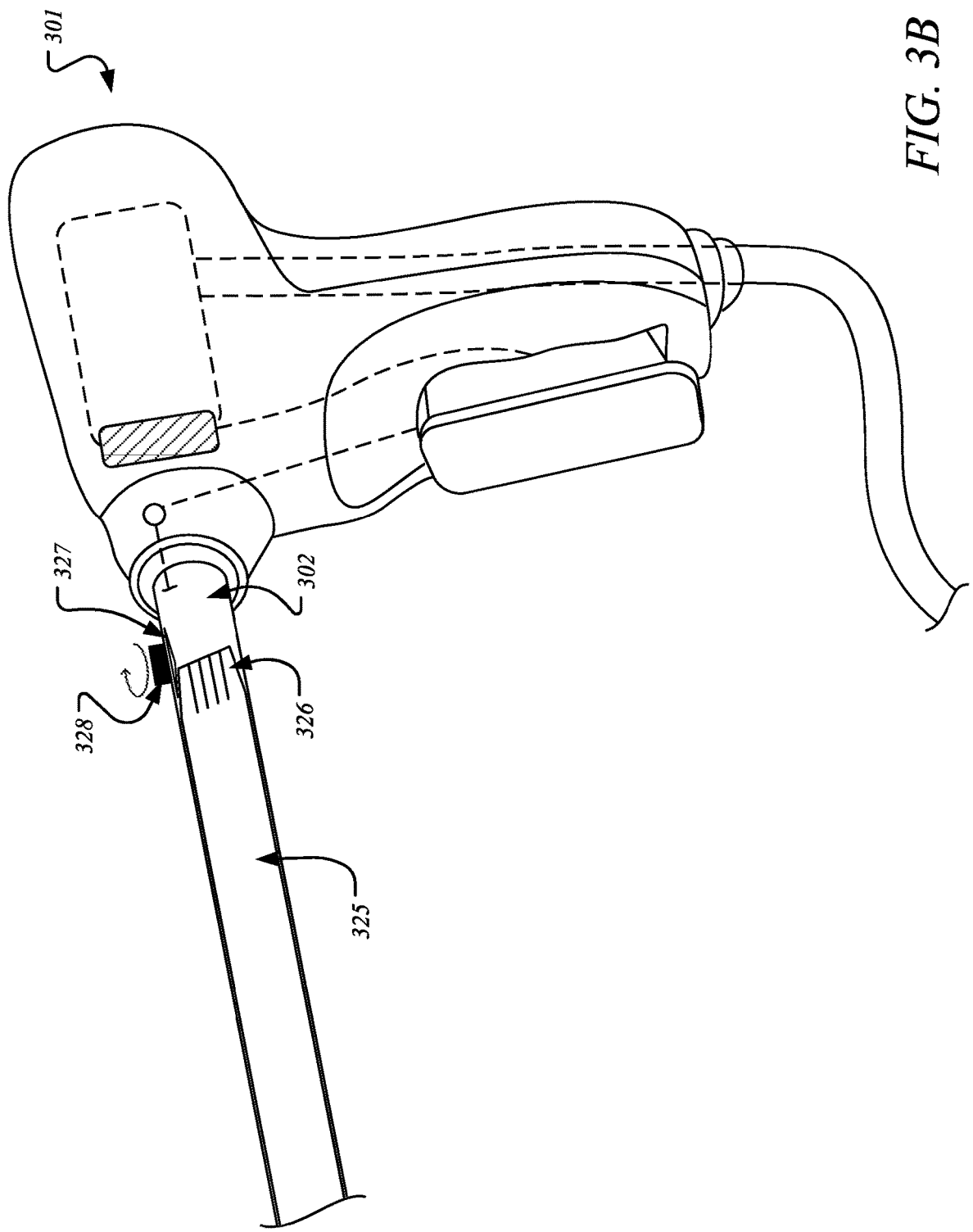
FIG. 3B is an exemplary illustration of a coupler of the surgical tool, according to an embodiment of the present disclosure.

Further, as seen in FIG. 3B, the coupler 325 can be rotatable via manual rotation by the user or via mechanical gears disposed near the handle of the surgical tool that controls the orientation of the coupler 325 relative to the hollow tube 302. In an embodiment, the coupler 325 extends the length of the hollow tube 302 to the handle 301. The proximal end of the coupler 325, near the handle 301, is fabricated to include a splined surface 326 or similar construct, known in the art, to function similar to a gear. A gear 327 arranged perpendicularly to the splined surface 326 and in position to drive the splined surface 326 is disposed so as to be controlled by a rotary knob 328, or similar control knob, on the surface of the hollow tube 302. When desired by the user, or as informed by acquired images of the surgical site, the user may rotate the head element 303 of the surgical tool by operating the rotary knob 328 on the surface of the hollow tube 302. According to an embodiment, the rotary knob 328 is disposed on the handle 301. The rotary knob 328 may further comprise indicia informing the user of the orientation of the head element 303 of the surgical tool. In an embodiment, the head element 303 of the surgical tool can be rotated clockwise, counter-clockwise, or in both directions as desired by the user. In another embodiment, rotational control of the coupler 325, and head element 303 therein, can be completed with digital control according to user input via a user interface located on the handle or external to the surgical tool.

Figure 4C:
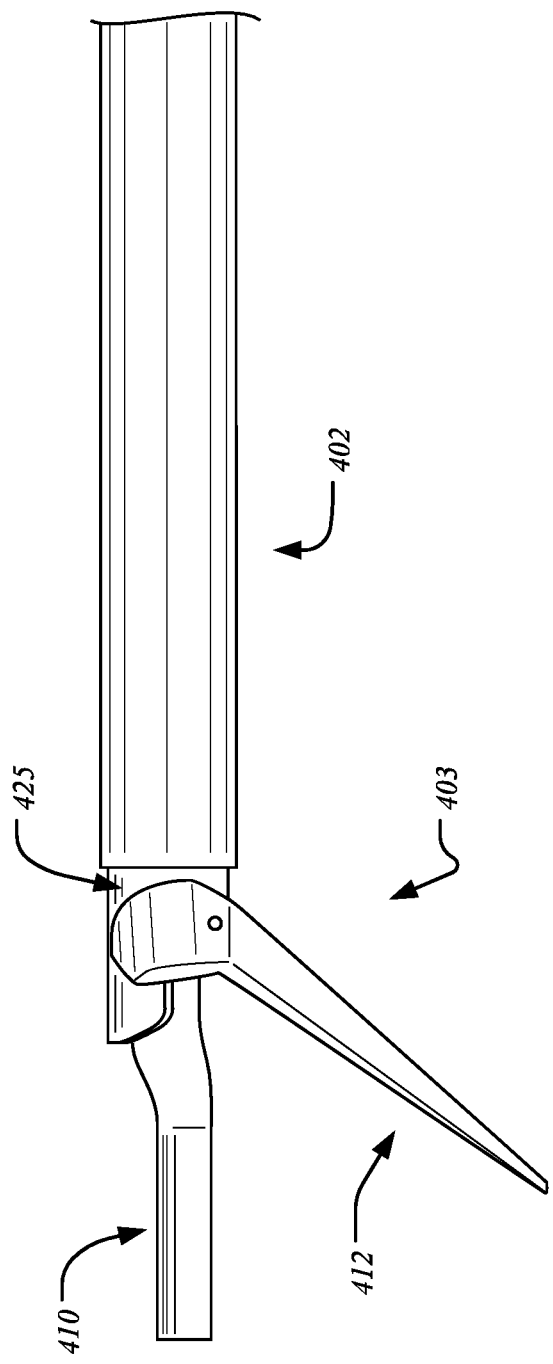
FIG. 4C is an exemplary illustration of an orientation of the head element of the surgical tool, according to an embodiment of the present disclosure.

In an embodiment, and as seen in FIGS. 4A-D, the head element of the surgical tool is rotatable about the long axis of the hollow tube via the coupler. FIG. 4A and FIG. 4B are exemplary illustrations of orientations of the head element of the surgical tool, according to an embodiment of the present disclosure. At a 0° orientation in FIG. 4A, the hollow tube 402, carrying the jaw wire and steam channel, is in line with the head element 403 of the surgical tool, disposed on the coupler 425. In this orientation, the movable jaw 412 and the hollow blade 410 are vertically aligned with the long axis of the hollow tube 402. The coupler 425 is rotatable about the long axis of the hollow tube as described above.

FIG. 4B reflects a 90° orientation of the head element 403 with respect to the hollow tube 402. In this orientation, following counter-clockwise rotation of the coupler 425, the hollow blade 410 and the movable jaw 412 are perpendicular to the vertical alignment of the 0° orientation.

Figure 4D:
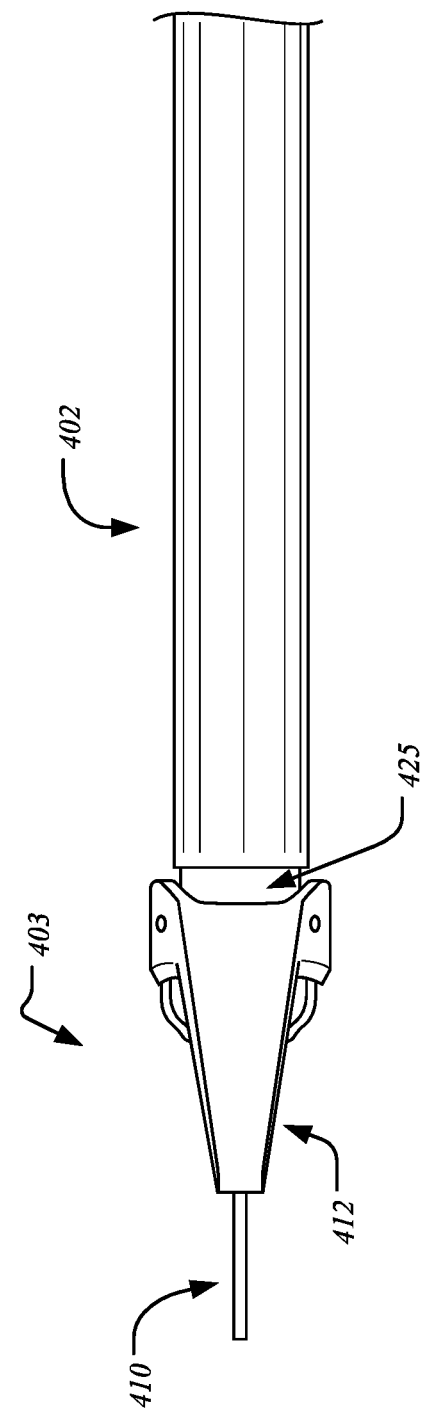
FIG. 4D is an exemplary illustration of an orientation of the head element of the surgical tool, according to an embodiment of the present disclosure.

FIG. 4C and FIG. 4D are additional exemplary illustrations of orientations of the head element of the surgical tool, according to an embodiment of the present disclosure. FIG. 4C reflects a 180° orientation of the head element 403 with respect to the hollow tube 402. In this orientation, following counter-clockwise rotation of the coupler 245, the hollow blade 410 and the movable jaw 412 are aligned with the vertical axis of the hollow tube 402.

FIG. 4D reflects a 270° orientation of the head element 403 with respect to the hollow tube 402. In this orientation, following counter-clockwise rotation of the coupler 425, the hollow blade 410 and the movable jaw 412 are perpendicular to the vertical alignment of the 0° orientation.

According to an embodiment, the coupler 425 is rotatable about the long axis of the hollow tube 402 in the clockwise direction, counter-clockwise direction, or a combination thereof. The ability to rotate the head element of the surgical unit provides the user with flexibility during surgical procedures. For example, with the head element in a 0° orientation, a tissue of interest may be just beyond the workable space of the surgical tool. Concurrently, there may be insufficient space to maneuver the length of the hollow tube to access the tissue of interest. However, with the ability to rotate the head element of the surgical tool about the axis of the hollow tube, the previously unreachable tissue of interest may now be accessible.

Figure 5A:
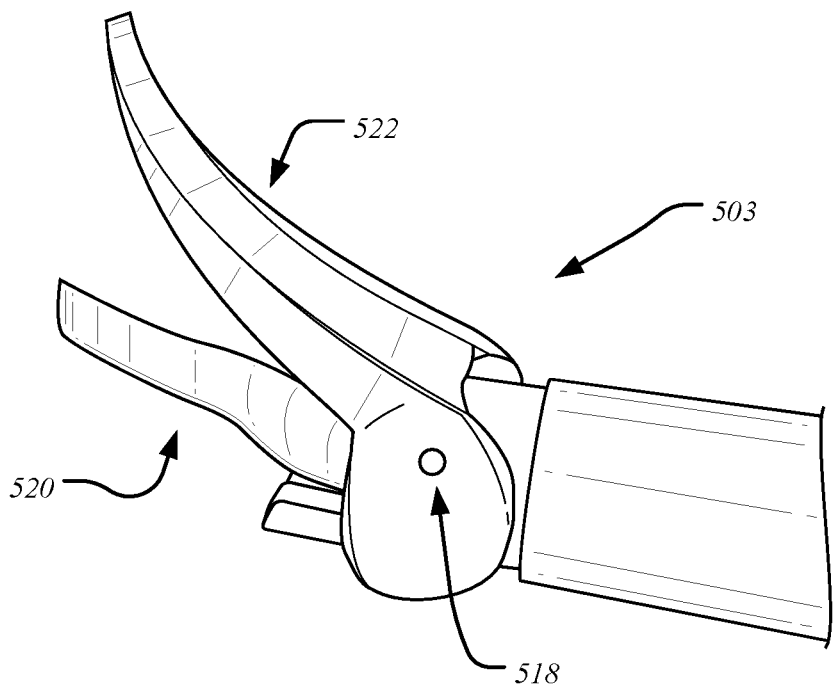
FIG. 5A is an exemplary illustration of a curvature of the head element of the surgical tool, according to an embodiment of the present disclosure.
Figure 5B:
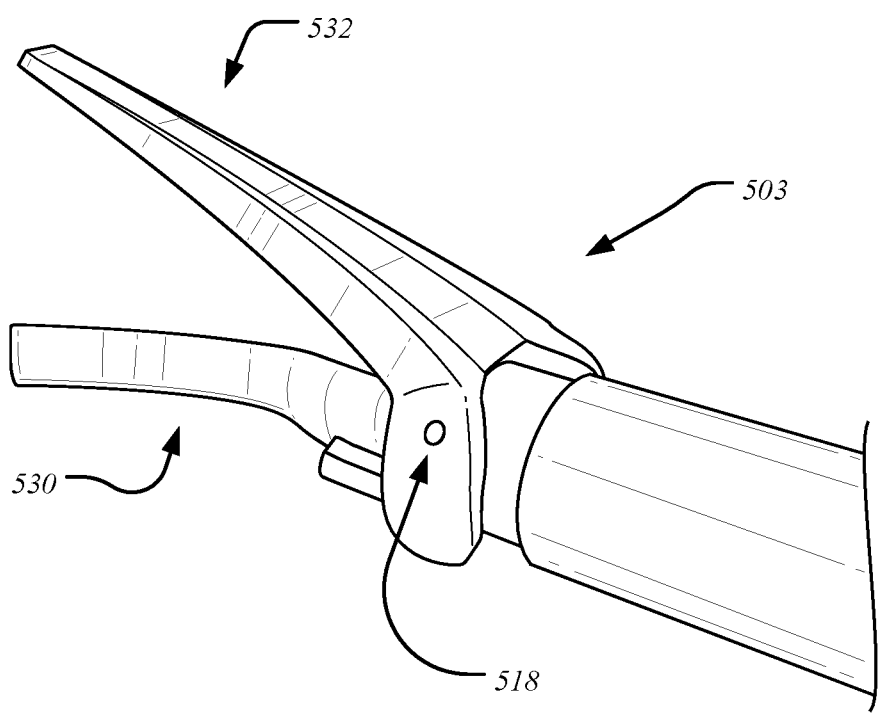
FIG. 5B is an exemplary illustration of a curvature of the head element of the surgical tool, according to an embodiment of the present disclosure.

In addition to rotation of the head element of the surgical tool about the long axis of the hollow tube, FIG. 5A and FIG. 5B are exemplary illustrations of curvatures of the head element of the surgical tool, according to an embodiment of the present disclosure. In FIG. 5A, the movable jaw 522 and the hollow blade 520 are illustrated in a curved embodiment, wherein the curve is a right curve extending from the base of the movable jaw 522 at the pin 518. The hollow blade 520 is curved in order to be congruent with the movable jaw 522 when in contact. In FIG. 5B, the movable jaw 532 and the hollow blade 530 are illustrated in a curved embodiment, wherein the curve is a left curve extending from the base of the movable jaw 532 at the pin 518. The hollow blade 530 is curved so as to be congruent with the movable jaw 532 when in contact.

In an embodiment, regarding FIG. 5A and FIG. 5B, the head element 503 can be fabricated to impart a desired curvature. The radius of curvature can be pre-determined according to a type of procedure to be performed. For example, if a procedure is to involve resection of a polyp from the lining of the colon, wherein access to a polyp may be restricted, an approach normal to the wall of the colon may be appropriate. In this instance, a straight cutting implement is sub-optimal for efficient resection, and, therefore, a curved head element 503 may be advantageous.

According to an embodiment, the radius of curvature can be imparted upon the head element 503 of the surgical tool following the initialization of a procedure. In an embodiment, the head element 503, and movable jaw 522, 532 and hollow blade 520, 530 therein, can be constructed of a semi-rigid yet flexible material that can elastically bend in accordance with the desired curvature of the head element 503. In an embodiment, the material is a linear elastic material and has a compressive elastic modulus relatively greater than a tensile elastic modulus of the material. One or more wires can be added to the length of the hollow tube and connected to opposing internal surfaces of each component of the head element 503, the movable jaw 522, 532 and the hollow blade 520, 530. One or more triggers can be added to the handle of the surgical tool to operate the one or more wires connected to opposing surfaces of each component of the head element 503. During operation, when it is desired to impart a curve in the movable jaw (and the hollow blade similarly), an engaged trigger can apply tension to a first of the one or more wires attached to an internal surface of the movable jaw. Tension induces compression in one face of the movable jaw and tension in the other, resulting in bending of the movable jaw toward the face under compression. Similarly, by applying tension to the second of the one or more wires attached to an internal surface of the movable jaw, a curvature in the opposite direction can be achieved. As the movable jaw 522, 532 and hollow blade 520, 530 are fabricated of a linear elastic material, imparted curvature in the component is dependent on the force applied to the one or more internal wires, allowing the user to control the curvature of the head element 503 according to the needs of a procedure.

In another embodiment, control of the curvature of the head element 503, and movable jaw 522, 532 and hollow blade 520, 530 therein, can be completed with digital control according to user input via a user interface located on the handle or external to the surgical tool.

In an exemplary embodiment, a user identifies, during a procedure, a need to reposition the head element of the surgical tool to access a target tissue. Instead of removing and reinserting the tool in order to access the target tissue, introducing the risk of further injury to neighboring tissues, the user may engage a one or more triggers that impart a curvature in the head element 503 components, providing the user greater flexibility and improving outcomes in surgical procedures.

FIG. 6A, FIG. 6B, FIG. 6C, and FIG. 6D are exemplary illustrations of non-limiting configurations of steam ports of a hollow blade of the surgical tool, according to embodiments of the present disclosure. In each Figure, the centerline indicates a cutting implement 611 of the hollow blade 610. In FIG. 6A, the plurality of steam ports 635 are substantially rectangular and are of identical sizes along the length of the hollow blade. In FIG. 6B, the plurality of steam ports 636 are substantially rectangular and are of identical sizes along the length of the hollow blade. Compared with FIG. 6A, the plurality of steam ports 636 in FIG. 6B are of relatively increased length and relatively increased width, as might be expected in accordance with a specific procedure. The steam ports 637 in FIG. 6C are substantially rectangular in shape and of alternating sizes along the length of the hollow blade. In FIG. 6D, the plurality of steam ports 638 are substantially circular and are of identical sizes along the length of the hollow blade.

The size, shape, number, and spatial arrangement of the steam ports are determined in accordance with the requirements of the desired procedure in order to deliver the appropriate steam flow parameters to the target tissue.

In another embodiment, the size and the shape of the hollow blade is modified according to the demands of the desired procedure. The length, width, and cross-sectional shape, in a non-limiting manner, may be modified as necessary.

According to an embodiment, the steam flow rate exiting the hollow blade is controlled by the size and the shape of the steam ports. For example, assuming a constant flow rate exiting the steam canister of the handle, a smaller aperture steam port in the hollow blade will increase the velocity at which the steam flow is exiting the hollow blade. In order to decrease the velocity of the steam flow exiting the hollow blade, a larger aperture steam port is required. In this way, steam port size and shape are determined according to tissue type and the appropriate flow parameters defined therein. The abovementioned embodiments should be considered non-limiting and are merely exemplary of a variety of possible implementations of the present disclosure.

FIG. 7A, FIG. 7B, FIG. 7C, and FIG. 7D are exemplary illustrations of configurations of a movable jaw of the surgical tool, according to an exemplary embodiment of the present disclosure. In each Figure, grips are disposed on the face of the movable jaw 715 so as to come into contact with a tissue of interest and control the motion of the tissue of interest during incision via the cutting implement of the hollow blade. In an embodiment, the grips are protrusions. In FIG. 7A, the grips 745 are substantially hemispherical in shape and are distributed evenly along the face of the movable jaw 715. In FIG. 7B, the grips 746 are substantially triangular, resembling teeth, and are distributed evenly along the length of the face of the movable jaw 715. The size and depth from the face of the movable jaw 715 of the grips can be modified to suit the desired application. According to an embodiment, in FIG. 7C, the grips 747 are substantially rectangular and are distributed evenly along the length of the face of the movable jaw 715. In FIG. 7D, the grips 748 are substantially rectangular in shape and are evenly distributed along the face of the movable jaw 715. The grips 748, however, are at a depth relatively increased compared with the grips 747 of FIG. 7C.

In another embodiment, the grips may be depressions. For example, with reference to FIG. 7A, a trough of substantially hemispherical shape may be disposed on the face of the movable jaw, thereby providing assistance in tissue control.

The size, shape, number, and spatial arrangement of the grips are determined in accordance with the requirements of the desired procedure. The frequency and width of the grips, across the face of the movable jaw, may be variable and intermittent, as required. The abovementioned embodiments should be considered non-limiting and are merely exemplary of a variety of possible implementations of the present disclosure.

In another embodiment, the size and shape of the movable jaw can be modified according to the demands of the desired procedure. The length, width, and cross-sectional shape, in a non-limiting manner, may be modified so as to appropriately grip tissue as required by the procedure.

Figure 8B:
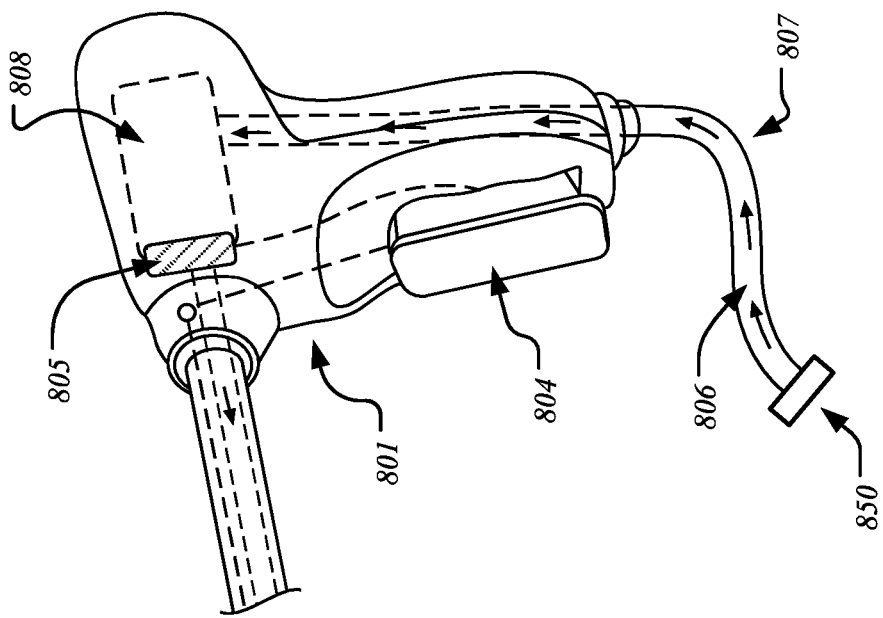
FIG. 8B is an exemplary illustration of a configuration of a control unit of a steam flow of the surgical tool, according to an exemplary embodiment of the present disclosure.
Figure 8A:
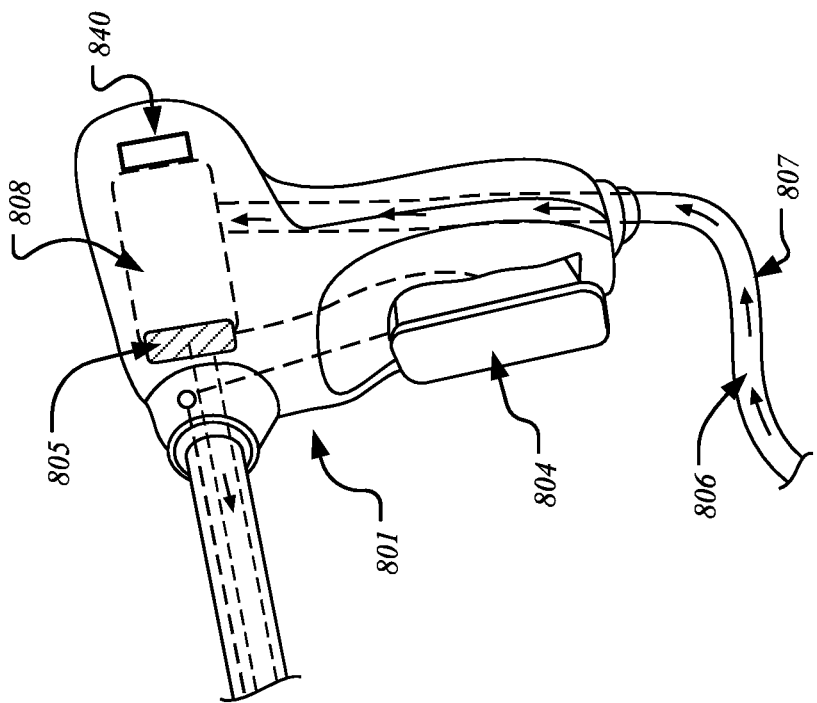
FIG. 8A is an exemplary illustration of a configuration of a control unit of a steam flow of the surgical tool, according to an exemplary embodiment of the present disclosure.

According to an embodiment, and in addition to potential modification to the abovementioned steam ports, the temperature of the steam flow may be controlled via internal or external control unit. FIG. 8A and FIG. 8B are exemplary illustrations of configurations of a control unit of a pressurized steam flow of the surgical tool, according to an exemplary embodiment of the present disclosure. In FIG. 8A, the control unit 840 is attached to the steam canister 808 of the handle 801 which is supplied by steam flow 806 from the steam tube 807. According to another embodiment, in FIG. 8B, the control unit 850 is located at the steam flow source and controls the temperature of the steam prior to sending the steam flow 806 to the steam canister 808. In each embodiment, and in a non-limiting manner, the control unit 840, 850 comprises a heating element and a thermostat configured to maintain temperature of a steam flow 806 in the steam canister 808.

According to an embodiment, power may be supplied to the control unit 840, 850, in a non-limiting manner, via rechargeable battery, conduction, induction or a combination thereof.

In an embodiment, the control unit 840, 850 includes a user interface for temperature adjustment. The user interface may include, but is not limited to, a display and a user interface mounted to the handle 801 or mounted externally at the control unit 850. In an embodiment, the user interface further comprises a mobile device, such as a smartphone, with a processing circuitry configured to communicate with the control unit 840, 850 and remotely control the thermostat, setting the temperature of the steam flow 806 in the steam canister 808 as appropriate for the desired procedure. In another embodiment, the user interface comprises a computer workstation with a processing circuitry configured to communicate with the control unit 840, 850 and remotely control the thermostat, setting the temperature of the steam flow 806 in the steam canister 808 as appropriate for the desired procedure.

Figure 9:
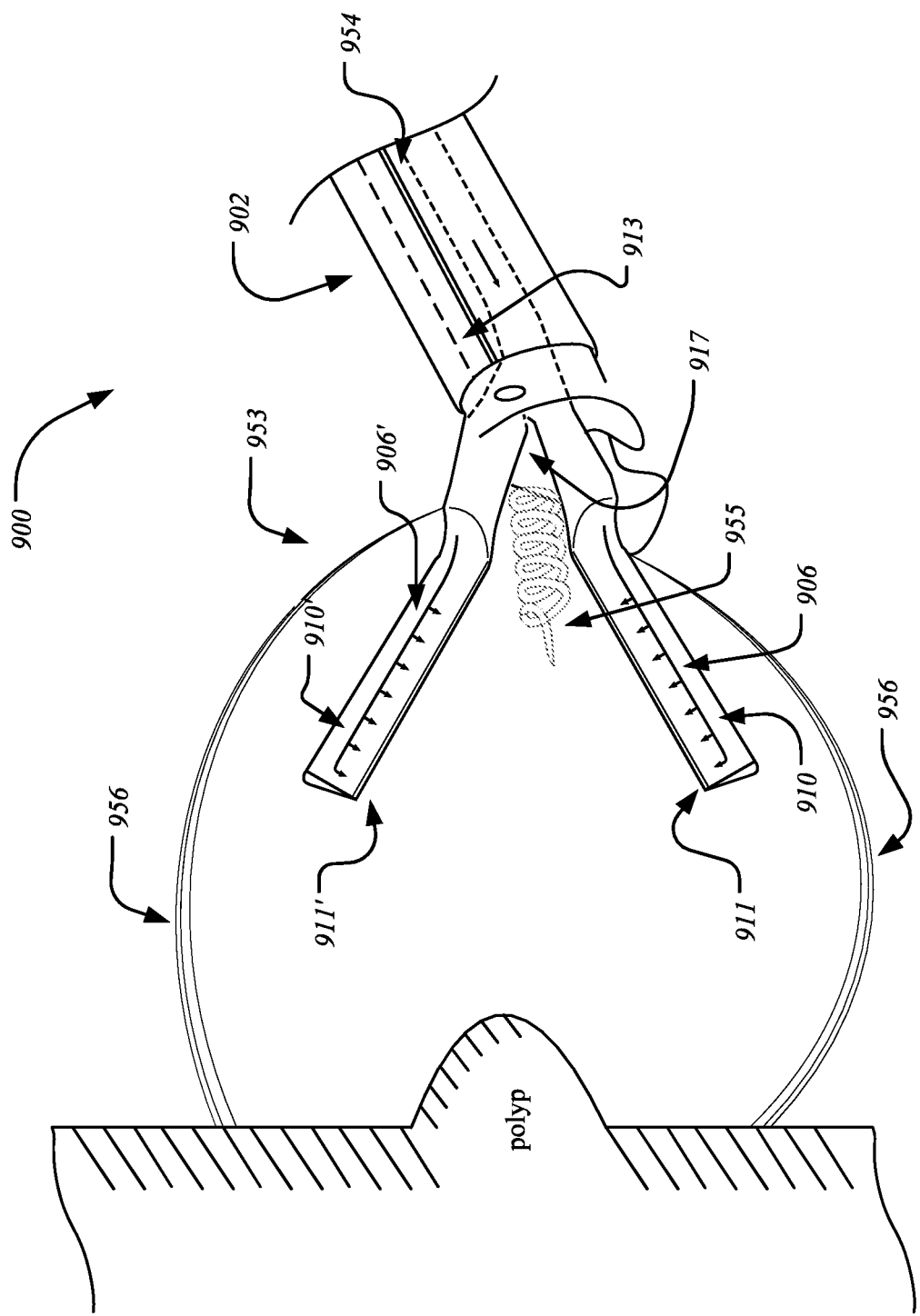
FIG. 9 is an exemplary illustration of a head element of the surgical tool, according to an exemplary embodiment of the present disclosure.

FIG. 9 is an exemplary illustration of a head element of a surgical tool interacting with a target tissue, or polyp, formed integrally within a tissue wall, according to an embodiment of the present disclosure. The head element 953 comprises two operative elements 910, 910', wherein the operative element 910' is rotatably connected to a jaw wire 913. The head element 953 further comprises a filter element 956 deployable from the basal surface of the operative elements 910, 910'. The filter element 956, when fully deployed, forms a three-dimensional cone around the target tissue and prevents the escape of large debris released from the target tissue during incision or ablation with an ablative agent. The filter element may be fabricated from a synthetic material of the kind typically used for embolic filters, such as polytetrafluoroethylene, with a pore size appropriate for the surgical procedure and ablative agent parameters. Such fabrication and use of filters for biological debris is understood in the art, as evidenced by U.S. Pat. No. 6,558,405 B1, which is incorporated herein by reference.

Each operative element 910, 910' comprises a cutting implement 911, 911' and ports 906, 906' for delivery of the ablative agent to the target tissue. The surgical tool 900 further comprises a latching element 955 extending from the hollow tube exit 917 of the hollow tube 902. The latching element 955 can be digitally- or manually-controlled from a user interface at the handle of the surgical tool 900. In an embodiment, the latching element 955 is substantially helical in structure, however, the shape of the latching element 955 can be any that is suitable for grasping and holding tissue. The latching element 955 is in connection with the handle of the surgical tool 900 via a latching element shaft 954. In an embodiment, the latching element shaft 954 is a threaded shaft with similarly threaded mating elements at the proximal end and the distal end of the surgical tool. During operation, with the filter element previously deployed, the latching element 955, controlled by a user via latching element shaft 954, is advanced into latching connection with the target tissue, at which time the cutting implement, ablative agent, or a combination thereof is engaged with the target tissue. Follow excision of the tissue by the operative elements, larger debris collected by the filter element 956 and the latched target tissue are removed from the surgical site with the surgical tool 900.

In another embodiment, the surgical tool 900 further comprises a suction element disposed at the hollow tube exit 917 of the hollow tube 902 for expedited removal of excised tissues via vacuum.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus, comprising:
a handle, disposed at a proximal end of the apparatus, including a reservoir for storage of an ablative agent, wherein the reservoir has a valve disposed at an exit end of the reservoir and a vapor feed line connected to an inlet end at a bottom of the handle;
a coupler connected to the handle and a hollow tube, wherein the hollow tube is configured to connect the coupler to the handle at the exit end of the reservoir, the coupler having a splined surface;
wherein the hollow tube is adjacent to the handle and arranged to be in fluid communication with the reservoir in the handle, wherein the hollow tube is connected to the exit end of the reservoir through the coupler;

a rotary knob disposed on the hollow tube at an end proximal to the coupler and configured to mechanically engage with the splined surface of the coupler to rotate the coupler about a longitudinal axis;

a head element, disposed at a distal end of the hollow tube, wherein the head element includes an operative element and an assisting element, wherein the operative element comprises a single hollow blade having a plurality of apically disposed ports in fluid communication with the hollow tube and configured to pass the ablative agent, a first wire extending from a trigger mounted on the handle and connecting to the operative element, a second wire extending from the trigger to the assisting element, wherein, on engagement, the trigger is configured to simultaneously mechanically retract the assisting element towards the operative element and mechanically open the valve to release the ablative agent from the reservoir into the hollow tube, and wherein the assisting element is a single assisting element that is a single jaw having an apical surface and a basal surface, the basal surface configured to contact the operative element when retracted by operation of the trigger.

2. The apparatus according to claim 1, wherein the assisting element includes an arrangement of one or more protrusions, depressions, or a combination thereof, disposed on the basal surface.

3. The apparatus according to claim 1, wherein the head element is substantially linear.

4. The apparatus according to claim 1, wherein the single hollow blade having the plurality of apically disposed ports is configured to release the ablative agent on opposing surfaces of the blade.

5. The apparatus according to claim 1, wherein the head element deforms in response to a force applied to the first wire and the second wire at the proximal end of the apparatus, the deformation in the head element producing a curvature in the operative element and the assisting element.

6. The apparatus according to claim 1, wherein the ablative agent includes steam.

7. The apparatus according to claim 1, further comprising a temperature control unit for controlling the temperature of the ablative agent, the temperature control unit comprising a heating element and a thermostat.

8. The apparatus according to claim 1, wherein the coupler is concentric with the hollow tube and has an outer diameter smaller than an inner diameter of the hollow tube.

* * * * *